United States Patent [19]

Mathewson

[11] Patent Number: 5,290,236
[45] Date of Patent: Mar. 1, 1994

[54] LOW PRIMING VOLUME CENTRIFUGAL BLOOD PUMP

[75] Inventor: Wilfred F. Mathewson, Bonsall, Calif.

[73] Assignee: Baxter International Inc., Deerfield, Ill.

[21] Appl. No.: 918,721

[22] Filed: Jul. 21, 1992

Related U.S. Application Data

[63] Continuation-in-part of Ser. No. 765,307, Sep. 25, 1991, Pat. No. 5,242,383.

[51] Int. Cl.$^5$ .................................... A61M 5/142
[52] U.S. Cl. .................... 604/131; 415/206; 604/151
[58] Field of Search ............... 415/200, 201, 202, 203, 415/204, 205, 206; 604/131, 151

[56] References Cited

U.S. PATENT DOCUMENTS

| | | |
|---|---|---|
| 312,788 | 2/1885 | Yellott . |
| 700,224 | 5/1902 | McRae . |
| 865,900 | 9/1907 | Hunsaker . |
| 1,022,425 | 4/1912 | Kuechler . |
| 1,372,532 | 3/1921 | Monberg . |
| 1,986,836 | 1/1935 | MacNeille ............ 415/206 X |
| 2,636,442 | 4/1953 | Roth ..................... 415/203 X |
| 3,489,340 | 1/1970 | Holzhausen ......... 415/206 X |
| 4,253,798 | 3/1981 | Sugiura ................ 415/213 R |
| 4,826,401 | 5/1989 | Clark et al. .......... 415/206 X |
| 5,017,103 | 5/1991 | Dahl ..................... 417/420 |
| 5,106,263 | 4/1992 | Irie ........................ 415/206 |

FOREIGN PATENT DOCUMENTS

| | | |
|---|---|---|
| 0205105 | 12/1986 | European Pat. Off. . |
| 0244844 | 11/1987 | European Pat. Off. . |
| 0467234A2 | 7/1991 | European Pat. Off. . |
| 3843428A1 | 12/1988 | Fed. Rep. of Germany . |
| 4015331A1 | 5/1990 | Fed. Rep. of Germany . |
| 2468772 | 6/1980 | France . |
| 1336494 | 7/1971 | United Kingdom . |
| 1523972 | 1/1976 | United Kingdom . |
| 2160932A | 6/1985 | United Kingdom . |
| 2187232A | 2/1987 | United Kingdom . |

Primary Examiner—Robert A. Hafer
Assistant Examiner—Sam Rimell
Attorney, Agent, or Firm—Bruce M. Canter

[57] ABSTRACT

A low priming volume centrifugal pump comprising a disc shaped impeller having opposite faces and an inlet hole centrally disposed therein. The impeller has flow channels disposed on at least one of the faces of the impeller which radiate outward from said inlet hole. The volume of the flow channels is small relative to the total impeller envelope volume providing for efficient momentum transfer with a minimum of turbulence and backflow Thus, priming volume is reduced and flow within the pump is more efficient. The pump can be used as stand alone device, or it can be integrated with a blood oxygenator into a common housing.

47 Claims, 3 Drawing Sheets

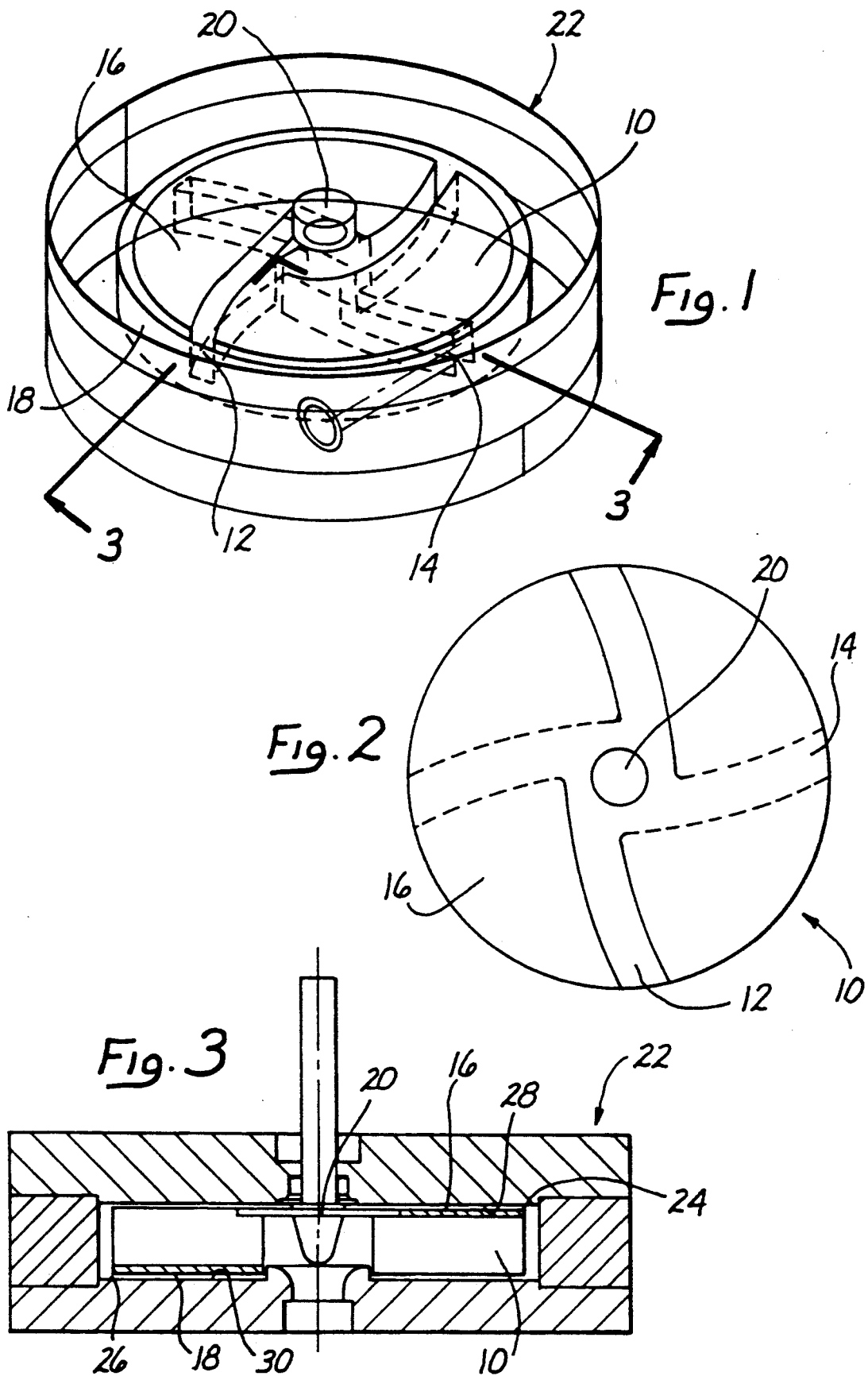

LOW PRIMING VOLUME CENTRIFUGAL BLOOD PUMP

RELATED CASES

This application is a continuation-in-part of U.S. application Ser. No. 07/765,307, filed on Sep. 25, 1991, now U.S. Pat. No. 5,292,383, for Integrated Low Priming Volume Centrifugal Pump And Membrane Oxygenator, which is incorporated herein as though fully set forth.

FIELD OF THE INVENTION

The invention relates to extracorporeal device technology for the support of patients during open heart surgery and in emergency situations requiring extracorporeal cardiac or cardiopulmonary support. In particular, the invention relates to new and useful improvements in apparatus for the pumping of blood to temporarily replace the cardiac function of a patient. Specifically, the invention relates to a centrifugal blood pump which can be used either as a stand alone blood pumping device in an extracorporeal circuit, or as a component of an integrated blood pump/blood oxygenator assembly.

BACKGROUND OF THE INVENTION

During open heart surgery and in some emergency cardiac or cardiopulmonary situations, it is necessary to have some means for pumping the blood either alone or in conjunction with an oxygenator to replace or support the patient's cardiac or cardiopulmonary functions.

Prior art extracorporeal device technology has used individual devices for the functions of pumping blood and oxygenating blood. Historically, the roller pump has been the blood pump of choice for extracorporeal circulation, mainly due to its reasonably low levels of blood damage and priming volume. However, because it is a positive displacement pump, high, unsafe pressures can develop if the discharge line is inadvertently closed off or restricted. Furthermore, the drive mechanism and motor is relatively cumbersome, making it less than ideal in terms of ease of use.

Recently, the centrifugal pump has come into some favor, primarily because it is safer and easier to use. It is safer because it is not a positive displacement pump, and it is easier to use because its drive mechanism and motor cam be made compact and relatively mobile. Early centrifugal blood pumps had vaneless impellers, and momentum was transferred via viscous drag between the impeller surfaces and the blood. Although these had the potential to decrease blood damage, relatively large surface area was required, requiring a large priming volume.

More recently, centrifugal blood pumps with vaned impellers have been introduced in order to reduce priming volume. A recent example of such a pump is disclosed in U.S. Pat. No. 5,017,103, to Dahl. Although blood damage, as measured by red cell hemolysis, can be reduced to acceptable levels with pumps of this type, there is still some increase due to the turbulence created by the vanes. A further disadvantage results from the backflow, radially inward, which occurs in the fluid spaces between the vanes, thus decreasing the potential delivery pressure of the pump. Additionally, the overall inlet and channel volume of this pump is still large relative the impeller envelope volume. Thus, priming volume is still relatively high.

U.S. Pat. No. 4,253,798, to Sugiura, discloses a centrifugal pump which is not disclosed for use as a blood pump. The pump has an impeller comprising a main disc and a plurality of vanes which project axially from at least one side of the disc. A fluid passage is formed between each pair of adjacent vanes having a cross section that decreases as the flow passage projects radially outward. The reduced passage width is intended to decrease the fluid vortices in the passage to improve pump delivery at low flow rates. In order to create the radially decreasing passageway, it is necessary to have a large interior impeller diameter. Furthermore, since the pump has two flow inlets, the total inlet and passageway volume of this pump is large compared to the total impeller envelope volume. If the Sugiura pump is used to pump blood, it will require an excessively large priming volume. The pump also has ribs placed at the midpoint of the passageways to provide mechanical integrity. These ribs increase the potential for fluid spillage, increasing fluid turbulence and decreasing pump efficiency. This would create serious problems for pumping blood, due to the increased likelihood of blood damage.

Prior art blood pumps which are used in conjunction with an oxygenator are typically connected together in an extracorporeal tubing loop to receive venous blood from the patient and return arterial blood back to the patient. One of the problems with these types of devices, such as that shown in U.S. Pat. No. 3,183,908, has been that large amounts of blood are required to prime the oxygenator, the pump, and the tubing between the oxygenator and the pump.

Some attempts have been made to incorporate the pumping and oxygenation functions in a single device. For example, U.S. Pat. No. 3,841,837 discloses a blood oxygenator or dialyzer that achieves enhanced transfer through rotation of a cylindrically mounted membrane placed eccentrically inside a stator housing. Blood flows in the annular space between the rotor and the stator. Rotation causes a pumping action, thus causing pumping and oxygenation to occur simultaneously. All of these prior art devices have required relatively large amounts of fluid to prime the pump and oxygenator. There have also been difficulties with the safety and ease of use by the perfusionist. Furthermore, these devices can be quite costly to manufacture.

What is needed is a low priming blood pump which is safe, easy to use, and which causes minimal blood damage. What is further needed is a blood pump which can be readily integrated into a blood oxygenator housing. Such an invention is disclosed and claimed herein.

SUMMARY OF THE INVENTION

The present invention is directed to a low priming volume centrifugal pump which can be used as a stand alone blood pumping device, or which can be integrated with a blood oxygenator into a common housing. The pump is safe, easy to use, has minimal blood stagnation regions within the housing, and causes minimal blood damage.

The pump impeller of the present invention is a vaneless, solid disc disposed within an enclosed housing. The impeller has flow channels formed into at least one of its faces. In the center of the impeller is an inner diameter inlet hole which directs fluid through the channels, radially outward, by centrifugal forces when the impeller is rotated. Gaps are provided on either side of the impeller between the faces and the corresponding opposing housing surfaces. The overall inlet and channel volume is small relative to the total envelope volume of the impeller. The relatively small channels allow for efficient momentum transfer with a minimum of turbulence and backflow. Thus, priming volume is reduced without sacrificing efficiency.

In a preferred embodiment, the impeller has channels formed on both sides of the impeller and open to its faces. In order to prevent blood stagnation, the flow channels are open to the housing surfaces which oppose the impeller faces. In a preferred embodiment, the size of the gaps between the impeller faces and the opposing upper and lower housing surfaces is of particular importance. If the gap is too small, high shear stresses results in unacceptable blood damage, or hemolysis. If, on the other hand, the gap is too large, pump efficiency is lost. Thus, the gap is designed to maximize pump efficiency while minimizing blood damage.

In the centrifugal pump of the instant invention, the impeller channel angle is chosen to permit a lower pump drive RPM in order to deliver a specific flow at a specified back pressure. In a preferred embodiment, the impeller channel angle is thirty degrees to the radial, at the impeller outlet.

In one embodiment of the present invention, the total cross sectional area of the channels is kept at a minimum to reduce priming volume. In a preferred embodiment, the total number of channels is four, two per impeller face. In this embodiment, the channel width is approximately the same dimension as the channel height. This minimizes the wetted channel perimeter for a given cross sectional area, which is desirable in order to reduce flow resistance.

In another embodiment, eight channels are used with the width of the channels approximately equal to one-half the height. In yet another embodiment sixteen channels are used with the channel width equal to one-fourth the channel height. These latter embodiments would increase the wetted surface area but would also decrease fluid spillage into the gap.

In one embodiment, the vertical channel walls are ninety degrees to the impeller surfaces. In this embodiment, a radius is placed at the channel corners. In a preferred embodiment, the vertical walls of the channels are tapered sixty degrees and the channels have a full bottom radius. This increases the momentum transfer from the impeller by reducing spillage of fluid into the gap.

In an alternate embodiment, the open channel wall edges are square with the impeller surface. In a preferred embodiment of the present invention, the faces of the impeller are cambered at the channel edges to enhance the pumping action in this region.

In yet another embodiment of the present invention, the pump is integrated with an oxygenator into a common housing. The integrated pump and oxygenator assembly is more specifically disclosed and described in parent U.S. application Ser. No. 07/765,307, now U.S. Pat. No. 5,242,383, and reference is made thereto. In this embodiment, the channel height is tapered so that it gradually increases from the fluid inlet to the channel outlet. This enhances blood flow through the fiber bed while minimizing priming volume.

These and other objects and features of the present invention will become more fully apparent from the following description and appended claims taken in conjunction with the accompanying drawings.

BRIEF DESCRIPTION OF THE DRAWINGS

FIG. 1 is a perspective view a first embodiment of the centrifugal pump of the present invention, with the top of the pump removed and showing portions of the impeller in dotted lines;

FIG. 2 is a schematic top plan view of the impeller used in the pump of FIG. 1;

FIG. 3 is a sectional view taken along line 3—3 of FIG. 1;

DETAILED DESCRIPTION OF THE INVENTION

Figure 4:
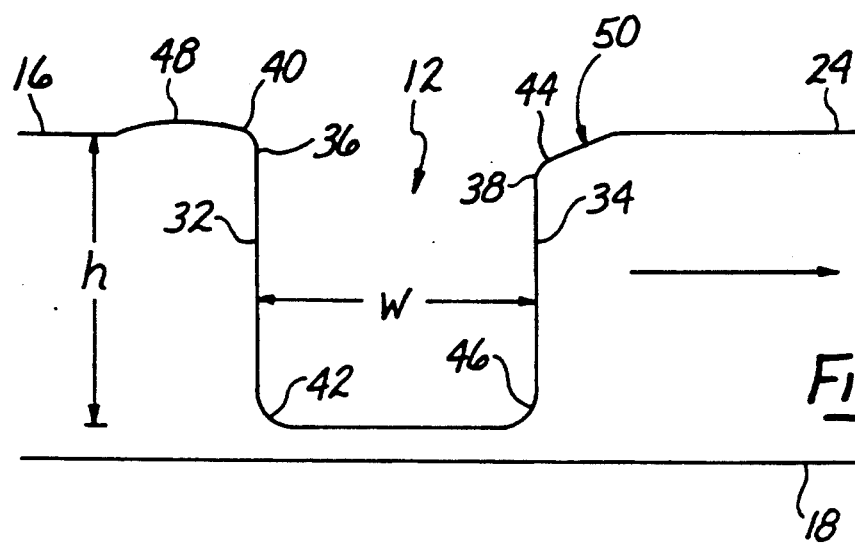
FIG. 4 is an enlarged end view of a first embodiment of the impeller of the present invention showing the novel features of the flow channel.

Reference is now made to the drawings wherein like parts have like numerals throughout. The detailed description set forth below in connection with the appended drawings is intended merely as a description of illustrative embodiments of the invention, and is not intended to represent the only form in which the present invention may be constructed or utilized. The description sets forth the construction and implementation of the invention in connection with the accompanying figures. It is to be understood, however, that the same or equivalent functions may be accomplished by different embodiments that are also intended to be encompassed within the spirit and scope of the invention.

FIG. 1 is a perspective view of a first embodiment of the centrifugal pump of the present invention, showing the impeller in dotted lines. FIG. 2 illustrates a top plan view of a first embodiment of the present invention. The centrifugal pump illustrated in FIGS. 1-3 comprises a solid disc shaped impeller 10 having flow channels 12 and 14 formed on faces 16 and 18 respectively. Channels 14 are depicted by dotted lines to indicate that they are disposed on bottom face 18. In this embodiment, there are two channels on each face. As illustrated in FIGS. 1 and 2, the channels 12 and 14 are alternately placed on either face 16 or 18. Impeller 10 has an inner diameter inlet hole 20 which directs fluid radially outward through flow channels 12 and 14, by centrifugal forces, when impeller 10 is rotated.

In a stand alone centrifugal blood pump used for cardiac support in adults, the preferred diameter for impeller 10 is between two and five inches. In a most preferred embodiment, the impeller diameter is three inches, the impeller thickness is approximately one-half inch and the diameter of inlet hole 20 is approximately eight-tenths of an inch.

The total volume of inlet hole 20 and channels 12 and 14 is small relative to the total envelope volume of impeller 10. This is in direct contrast to conventional radial impellers for centrifugal pumps. Conventional centrifugal pumps generally operate under higher flow rates for a given required delivery pressure. Such pumps typically have impellers with thin vanes and wide flow channels between the vanes, as in U.S. Pat. No. 5,017,103, to Dahl. This maximizes the flow channel volume to create high flow rates and to minimize fluid pressure in the channels. To date, centrifugal blood pumps have typically had this design due to the conventional wisdom that reducing channel size to increase fluid pressure could result in hemolysis, or blood cell damage.

The impeller diameter and RPM requirements of the pump of the present invention, on the other hand, are dictated by delivery pressure rather than flow demands. Furthermore, in hemolysis testing it has been found that the pump of the present invention exhibited a hemolysis level that is one-third the level of other centrifugal blood pumps. Thus, an unexpected result of the present invention has been the construction of a centrifugal blood pump with narrow flow channels that actually reduces hemolysis levels. It is now possible, in extracorporeal cardiac and cardiopulmonary support, to meet both the requirement of flow and pressure with low priming volume and minimal levels of hemolysis.

The relatively small channels 12 and 14 of the present invention allow for efficient momentum transfer with a minimum of turbulence and backflow. Impeller 10 of the present invention maintains high fluid delivery pressures at adequate flow rates, and thus allows the priming volume to be reduced while hemolysis levels are minimized. The volume of flow channels 12 and 14 should be of a size to permit relatively laminar flow of the fluid in impeller 10 so as to control friction losses and to minimize blood damage. Total flow channel volume, including channels 12 and 14 and inlet 20, is preferably between 5% and 50% of the total envelope volume. In a preferred embodiment, the total flow channel volume is between 10% and 40% of the total envelope volume. The flow channel volume can be altered by any means such as adjusting the size, shape and number of the flow channels.

In the preferred embodiment illustrated in FIGS. 2 and 3, impeller 10 has channels 12 and 14 on both of its faces 16 and 18. Impeller 10 is disposed within housing 22 having gaps 24 and 26 on either side of impeller 10 between faces 16 and 18 and the corresponding opposing upper and lower housing surfaces 28 and 30. In order to prevent blood stagnation, flow channels 12 and 14 are open to housing surfaces 28 and 30, respectively. In a preferred embodiment, the size of gaps 24 and 26 is of particular importance. If the gaps are too small, high shear stresses results in unacceptable blood damage, or hemolysis. If, on the other hand, the gap is too large, pump efficiency is lost. It has been determined that a gap size between 0.020 and 0.050 inches will maximize pump efficiency while minimizing blood damage. In a preferred embodiment, wherein a three inch impeller is run at a maximum RPM of 3,000, a gap of 0.040 inches is used.

In the present invention, the angle between impeller channels 12 and 14 and the radius of impeller 10 is designed to permit a lower pump drive RPM while delivering a specific flow at a specified back pressure. In one embodiment, the impeller channel angle is greater than zero and less than forty-five degrees. In a preferred embodiment, the impeller channel angle is thirty degrees from the impeller radius.

As was discussed above, the pump of the present invention has a reduced priming volume due to the reduced channel and inlet volume. The preferred number of flow channels is four, two per impeller face. This permits sufficient blood flow while minimizing the priming volume. In order to insure further reductions in priming volume, the total cross sectional area of the channels can be reduced. A flow channel of a preferred embodiment is illustrated in FIG. 4, wherein the channel width w is approximately equal to the channel height h. This minimizes the wetted channel perimeter for a given cross sectional area, which has the added advantage of reducing flow resistance.

In an alternate embodiment, eight flow channels are used, four per impeller face, with the width of the channels equal to approximately one-half the height. In yet another embodiment sixteen channels are used, eight per impeller face, wherein the channel width is equal to one-fourth the channel height. Although these latter embodiments would increase the wetted surface, they have the advantage of decreasing fluid spillage into the gaps. Other embodiments having various number of flow channels with appropriate corresponding cross sections could be designed by those skilled in the art and still remain within the spirit of the present invention.

In the embodiment of FIG. 4, the vertical walls 32 and 34 of flow channel 12 are at a ninety degree angle to the impeller surfaces. The direction of rotation, as depicted by the arrow, is from leading edge 36 of wall 32 to trailing edge 38 of wall 34. It is common for centrifugal pumps to have regions where fluid flow stagnates. This is of particular concern when pumping blood, due to the possible damage to the blood cells that this would entail. In order to reduce stagnant regions of blood flow a defined radius is placed at each of the corners of channel 12. In the embodiment of FIG. 4, a radius of 0.025 inches is placed at the top corner 40 of wall 32, at leading edge 36. A radius of 0.050 inches is placed at the bottom corner 42 of wall 32 and at the top corner 44 and bottom corner 46 of wall 34.

In an alternate embodiment of the present invention, the channel wall edges are square with the impeller surface (not shown). In a preferred embodiment, however, faces 16 and 18 of impeller 10 are cambered close to or at the channel edges. FIG. 4 shows camber 48 at leading edge 36. The maximum camber should be between 0.010 and 0.030 inches. In a preferred embodiment, camber 40 is 0.020 inches. A similar camber is placed at or near the leading edge 36 of each flow channel 12 and 14 on both faces of impeller 10. This results in a reduction in the size of gaps 24 and 26, in that region, from 0.040 to 0.020 inches, which enhances the pumping action.

Due to the structure of channels 12 and 14 and the direction of rotation of impeller 10, blood flows through the channels radially outward and in the direction from leading edge 36 to trailing edge 38, causing possible fluid separation in this region. This can be obviated by tapering trailing edge 38 to ensure a smoother flow path around edge 38. Trailing edge 38 will have a taper 50 between ten and forty-five degrees. In a preferred embodiment, taper 50 is approximately twenty degrees.

Figure 5:
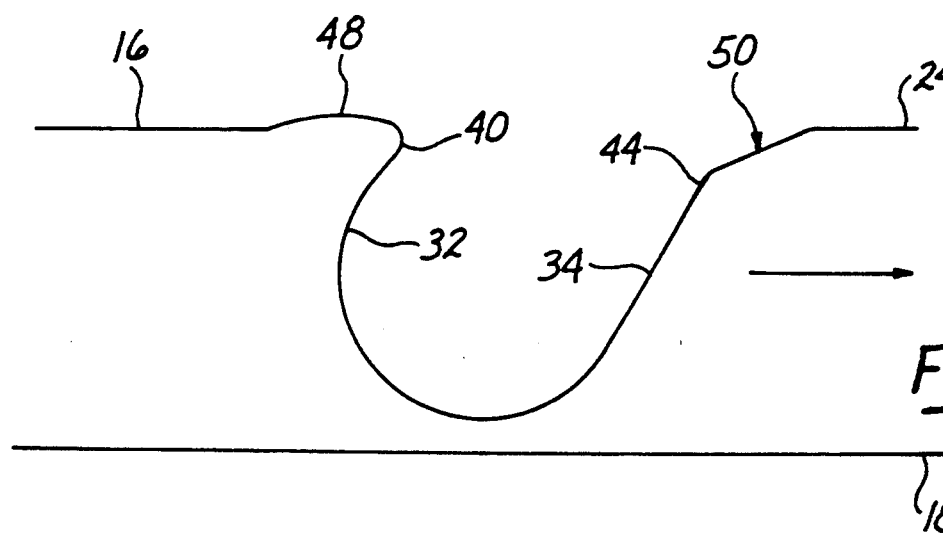
FIG. 5 is an enlarged end view of a second, preferred embodiment of the impeller of the present invention showing the novel features of the flow channel.

FIG. 5 illustrates the preferred channel geometry for the present invention. In this embodiment camber 48 is placed on faces 16 and 18, in the same dimensions discussed above with respect to FIG. 4. As in FIG. 4, a radius of 0.025 inches is placed at top corner 40 of wall 32, at leading edge 36, and a radius of 0.050 inches is placed at top corner 44 of wall 34, at trailing edge 38. Trailing edge 38 again has taper 50, which is approximately twenty degrees, to ensure a smoother flow path. However, unlike FIG. 4, vertical walls 32 and 34 of channels 12 and 14 are slanted sixty degrees and the channels have a full bottom radius. The preferred radius for the channel bottom is 0.020 inches. This particular channel geometry increases the momentum transfer from impeller 10 by reducing spillage of fluid into gaps 24 and 26.

Figure 6:
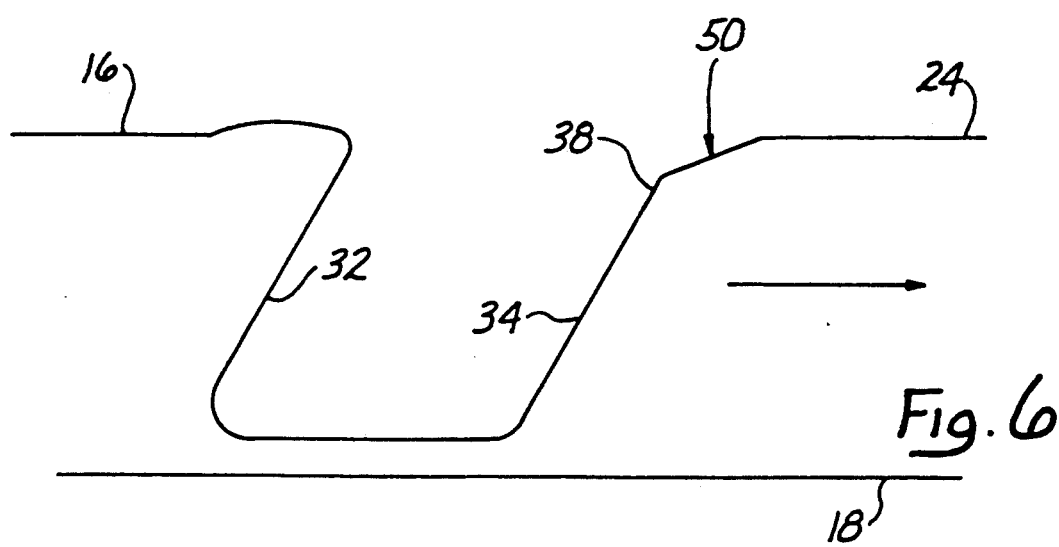
FIG. 6 is an enlarged end view of a third embodiment of the impeller of the present invention showing the novel features of the flow channel.

FIG. 6 illustrates yet another embodiment of the present invention wherein the channel geometry has again been modified to reduce stagnation and prevent fluid spillage. In this embodiment, channel walls 32 and 34 are again slanted at a sixty degree angle from the vertical to increase momentum transfer from impeller 10 to the fluid due to the fact that less fluid will spill into gaps 24 and 26. Like the embodiments of FIGS. 4 and 5, upper and lower faces 16 and 18 of impeller 10 are cambered, a radius is placed at the corners of walls 32 and 34, and trailing edge 38 is tapered at an angle of twenty degrees to ensure a smoother flow path. Unlike the embodiment of FIG. 5, however, the bottom of the channel is parallel to the impeller face.

It should be understood that other, similar modifications to the impeller and channel geometries could be made by those skilled in the art, and still remain within the scope of the present invention.

Figure 7:
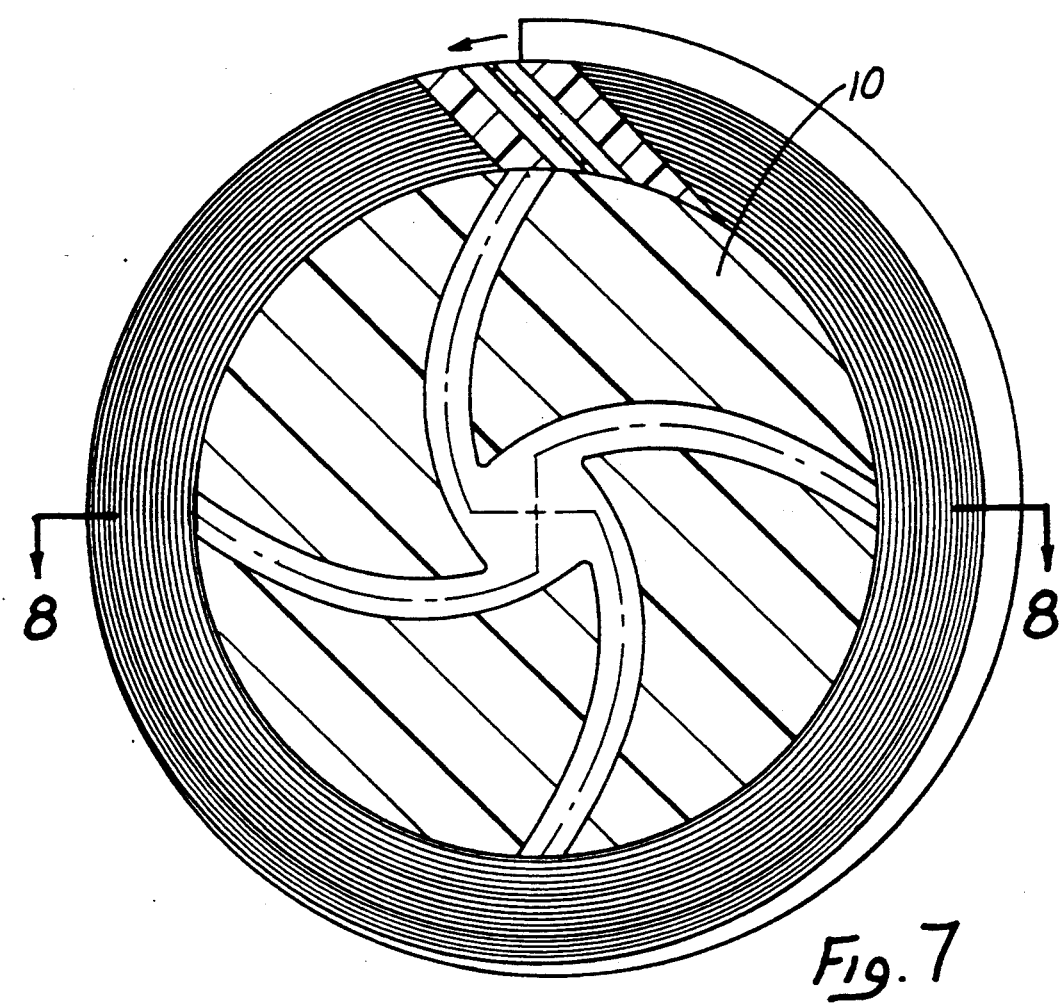
FIG. 7 is a schematic top plan view of the impeller of the present invention, integrated into a common housing with a blood oxygenator.
Figure 8:
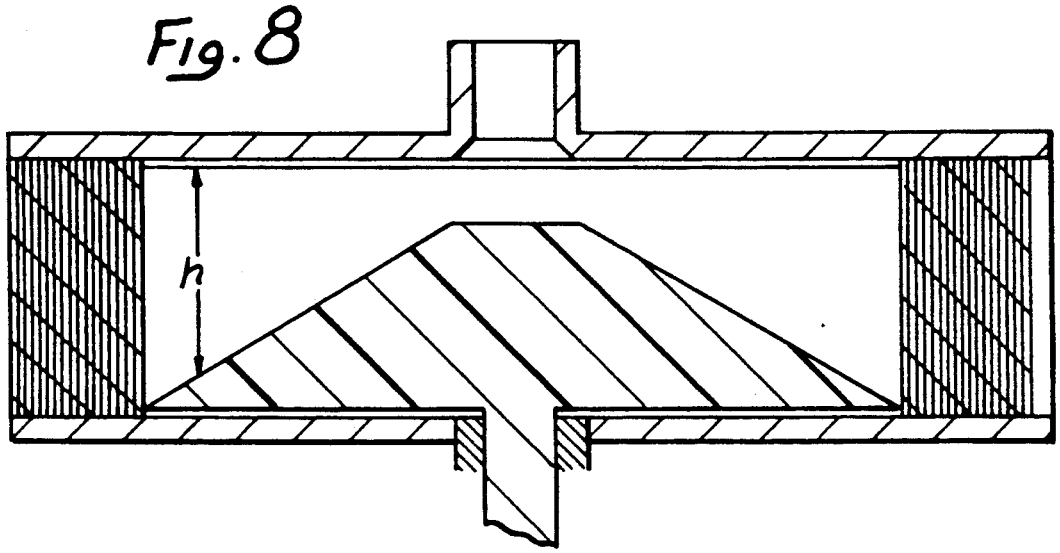
FIG. 8 is a sectional view taken along line 8—8 of FIG. 7.

In yet another embodiment of the present invention, as illustrated in FIGS. 7 and 8, the pump is integrated with an oxygenator into a common housing. The integrated pump and oxygenator assembly is more specifically disclosed and described in parent U.S. application Ser. No. 07/765,307, and reference is made thereto.

In this embodiment, for use on an adult, the impeller height is greater than one-half inch. As illustrated in FIG. 8, the channel height is tapered so that it gradually increases from the fluid inlet to the channel outlet, which enhances blood flow through the fiber bed, while keeping priming volume to a minimum.

While the preferred embodiments of my invention have here been shown and described, it is to be understood that I do not limit myself to the precise construction herein disclosed and that various changes and modifications may be made within the scope of the invention as defined in the appended claims.

I claim:

1. A low priming volume centrifugal blood pump comprising:
   a housing having an inlet;
   a disc shaped impeller enclosed within said housing, said impeller having first and second opposing faces and an inlet hole centrally disposed therein in fluid communication with said housing inlet;
   a gap between each of said impeller faces and the corresponding housing surface opposing said impeller face; and
   a plurality of flow channels, at least one of said flow channels disposed on and open to said first face and at least one of said flow channels disposed on and open to said second face, each of said flow channels radiating outwardly from and fluidly communicating with said inlet hole to a flow channel outlet, wherein the volume of said flow channels is small relative to the total impeller envelope volume.

2. The pump of claim 1 wherein the total volume of said inlet hole and said flow channels is about 5% to about 50% of the total impeller envelope volume available.

3. The pump of claim 2 wherein the total volume of said inlet hole and said flow channels is less than about 50% of the total impeller envelope volume available.

4. The pump of claim 2 wherein the total volume of said inlet hole and said flow channels is less than about 30% of the total impeller envelope volume available.

5. The pump of claim 1 having two flow channels on each of said impeller faces.

6. The pump of claim 1 having four flow channels on each of said impeller faces.

7. The pump of claim 1 having eight flow channels on said impeller face.

8. The pump of claim 1 wherein said flow channels are disposed from the radius of said impeller face, at the channel outlet, at an angle greater than zero and less than forty-five degrees.

9. The pump of claim 8 wherein said flow channels are disposed from the radius of said impeller face, at the channel outlet, at an angle of approximately thirty degrees.

10. The pump of claim 1, wherein said flow channels are disposed on both faces of said impeller.

11. The pump of claim 10 wherein said flow channels are alternately placed on opposite impeller faces.

12. The pump of claim 10 wherein two flow channels are disposed on each impeller face.

13. The pump of claim 12 wherein the width and height of said flow channels are approximately equal.

14. The pump of claim 10 wherein four flow channels are disposed on each impeller face.

15. The pump of claim 14 wherein the width of each of said flow channels is approximately one-half of the channel height.

16. The pump of claim 10 wherein eight flow channels are disposed on each impeller face.

17. The pump of claim 16 wherein the width of each of said flow channels is approximately one-fourth of the channel height.

18. The pump of claim 1 wherein the diameter of said impeller is between two and five inches.

19. The pump of claim 18 wherein the diameter of said impeller is three inches.

20. The pump of claim 1 wherein the thickness of said impeller is between 0.3 and three inches.

21. The pump of claim 20 wherein the thickness of said impeller is approximately one-half inch.

22. The pump of claim 1 wherein the diameter of said inlet hole is approximately eight-tenths of an inch.

23. The pump of claim 1 wherein the vertical surfaces of said flow channels are disposed at ninety degrees to the impeller face.

24. The pump of claim 1 wherein the vertical surfaces of said flow channels are at sixty degrees to the impeller face.

25. The pump of claim 24 wherein the bottom surface of said flow channels has a full radius.

26. The pump of claim 25 wherein said radius is approximately 0.020 inches.

27. The pump of claim 1 wherein each of said flow channels has a defined radius placed at its corners.

28. The pump of claim 27 wherein a radius of 0.025 inches is placed at one of the top corners of each of said flow channels.

29. The pump of claim 27 wherein a radius of 0.050 inches is placed at one of the top corners of each of said flow channels.

30. The pump of claim 27 wherein a radius of 0.050 inches is placed at both bottom corners of each of said flow channels.

31. The pump of claim 1 wherein each of the faces of said impeller having flow channels therein has a camber near the edge of each of said flow channels such that said the gap between said impeller face and said opposing housing surface varies between the flow channels.

32. The pump of claim 31 wherein the maximum dimension of said camber is between 0.010 and 0.030 inches.

33. The pump of claim 32 wherein the dimension of said camber is 0.020 inches.

34. The pump of claim I wherein the maximum dimension of said gap is between 0.020 and 0.050 inches.

35. The pump of claim 34 wherein the dimension of said gap is 0.040 inches.

36. The pump of claim 1 wherein each of said flow channels has a leading edge and a trailing edge and wherein the direction of the rotation of said impeller is from said leading edge to said trailing edge.

37. The pump of claim 36 wherein said trailing edge is tapered to assure a smoother flow path.

38. The pump of claim 37 wherein said trailing edge is tapered at an angle between ten and forty-five degrees.

39. The pump of claim 38 wherein said trailing edge is tapered at an angle of twenty degrees.

40. The pump of claim 1 wherein the height of said flow channels gradually increases from said impeller inlet hole to said flow channel outlet.

41. The pump of claim 1 wherein the ratio of height to width of each of said flow channels is between four to one and one to one.

42. The pump of claim 41 wherein said ratio is four to one.

43. The pump of claim 41 wherein said ratio is two to one.

44. The pump of claim 41 wherein said ratio is one to one.

45. A low priming volume centrifugal blood pump comprising:
   a housing having an inlet;
   a disc shaped impeller enclosed within said housing, said impeller having opposite faces and an inlet hole centrally disposed therein in fluid communication with said housing inlet;
   a gap between each of said impeller faces and the corresponding housing surface opposing said impeller face;
   a pair of flow channels disposed within each face of said impeller and open to said housing surfaces, each of said flow channels radiating outwardly from and fluidly communicating with said inlet hole to a flow channel outlet, each of said channels disposed from the radius of said impeller face, at said flow channel outlet, at an angle of approximately thirty degrees; and
   a camber near the edge of each of said flow channels such that said gap between said impeller face and said opposing housing surface varies between the flow channels;
   wherein the width and height of said flow channels are approximately equal and wherein the total volume of said inlet hole and said flow channels is less than 50% of the total impeller envelope volume.

46. The pump of claim 45 wherein the vertical surfaces of said flow channels are at sixty degrees to the impeller face and the bottom surface of said flow channels has a full radius.

47. The pump of claim 45 wherein a radius is placed at the top edges of each of said flow channels and one of said top corners is tapered.

* * * * *